United States Patent [19]

Okayama et al.

[11] Patent Number: 5,912,300

[45] Date of Patent: Jun. 15, 1999

[54] POLY-AMINO ACIDIC OLIGONUCLEOTIDE-CARRIER

[75] Inventors: Minenobu Okayama, Ibaraki; Yosuke Suzuki; Akira Wada, both of Saga, all of Japan

[73] Assignee: Hisamitsu Pharmaceutical Co., Inc., Saga, Japan

[21] Appl. No.: 08/619,564

[22] PCT Filed: Sep. 28, 1994

[86] PCT No.: PCT/JP94/01590

§ 371 Date: Jun. 6, 1996

§ 102(e) Date: Jun. 6, 1996

[87] PCT Pub. No.: WO95/09009

PCT Pub. Date: Apr. 6, 1995

[30] Foreign Application Priority Data

Sep. 28, 1993 [JP] Japan .................................. 5-241853

[51] Int. Cl.[6] .................................................. C08G 63/48
[52] U.S. Cl. ...................... 525/54.1; 525/54.11; 525/54.2
[58] Field of Search ................... 536/22.1, 23.1; 530/300, 350, 322, 395; 525/54.1, 54.11, 54.2; 527/200, 207; 528/328

[56] References Cited

U.S. PATENT DOCUMENTS 5,132,230 7/1992 Rosenthal et al. ...................... 436/15

OTHER PUBLICATIONS

Ca 122:38716, 1994.

*Primary Examiner*—Sheela Huff
*Attorney, Agent, or Firm*—Wenderoth, Lind & Ponack, L.L.P.

[57] ABSTRACT

The present invention provides a poly-amino acidic oligonucleotide-carrier comprising a poly-lysine:serine random copolymer.

This carrier is bonded with oligonucleotide without causing precipitation, and smoothly releases the bonded oligonucleotide within cells. It is therefore useful as an in vivo transport carrier of an oligonucleotide drug against various genetic diseases and viral diseases such as AIDS. It also makes a great contribution to creation of various useful animals and plants by genetic engineering technique, including virus-resistant plants.

6 Claims, 10 Drawing Sheets

5' - <u>GCC</u>GUC<u>CCCGG</u> -3'

Fig. 1(a)

5' - CGGCAAAGCCGGAAAGCCGGAGUAGUCGGGGC -3

Fig. 1(b)

Underscored portions represent DNA.

Lane 1   1E-5M   PLS
Lane 2   2E-5M   PLS
Lane 3   5E-5M   PLS
Lane 4   8E-5M   PLS
Lane 5   1E-4M   PLS

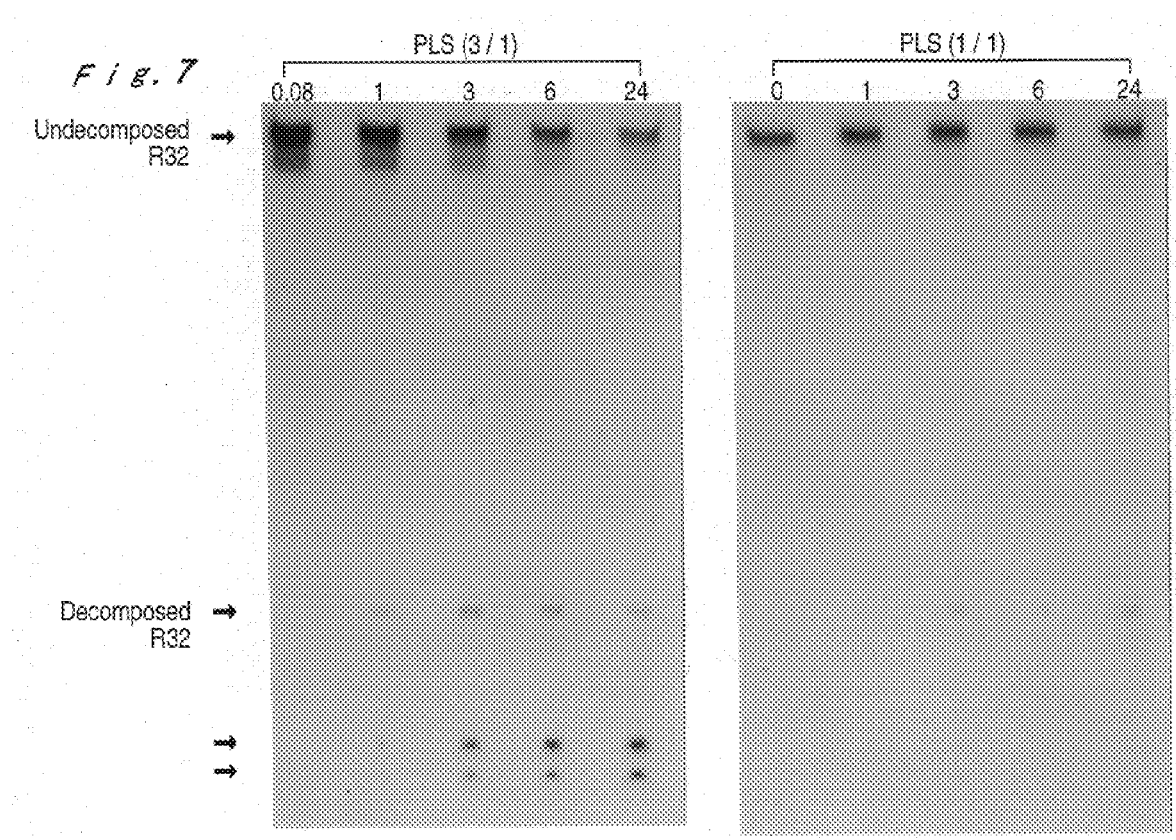

POLY-AMINO ACIDIC OLIGONUCLEOTIDE-CARRIER

TECHNICAL FIELD

The present invention relates to a poly-amino acidic oligonucleotide-carrier. More particularly, the present invention relates to a novel poly-amino acidic carrier for oligonucleotide, which carrier is useful when transporting a plasmid DNA vector which possesses a drug oligonucleotide to be incorporated into chromosome thereby expressing RNA of the oligonucleotide in cells, or a drug which contains, as an effective ingredient, oligonucleotide having a specific function against mRNA of viral gene.

BACKGROUND ART

Fundamental studies on medical use of oligonucleotide (for example, antisense oligomer) have recently been actively carried out, and are now entering a stage of concretely searching for potentiality thereof. Actually, there are available many reports of in vitro studies on oligonucleotide: stability against solvent, selection of a target gene sequence to antisense oligomer, membrane permeability in cell lines, life span, nuclease resistance, intercellular distribution and the like.

Along with the progress of these fundamental studies, it has come to be considered very important to select an appropriate carrier substance when using oligonucleotide as a medical drug, and development of such a carrier substance and solution of problems for this purpose are now becoming inevitable tasks. More specifically, for example, important problems for this carrier include exclusion of positive charge of carrier complex which is unfavorable in biological dynamics of administration pathways such as intravenous injection, establishment of an efficient targeting system including cell membrane permeability, and improvement of life span and stability of oligonucleotide drugs and improvement of uptake efficient into cells.

Since oligonucleotide itself is very unstable and susceptible to decomposition under the effect of external conditions, research efforts are actively made to develop a drug delivery carrier for stably and efficiently carrying oligonucleotide to a target organ.

Overview of the process of the past research and development demonstrates that many of the conventional carrier are based on liposome which is a structure having a lipid bilayer configuration similar to a biological membrane. For example, an oligonucleotide drug included in liposome is reported, in which the oligonucleotide is stable in liposome, and at the same time, chemical or cellular specificity of the oligonucleotide is increased by chemical modification from liposome (Alain R. Thierry and Anatoly Dritschils, Nucleic Acid Res., 20, 5691–5698(1992)).

However, fine particle of liposome have a demerit of having a short half-life in blood. To overcome this disadvantage, improvements have recently been made in chemical stability such as oxidation stability, biological stability and colloidal chemical stability, and a new-generation liposome having a long half-life and an immunoliposome (a liposome having an antibody imbedded onto the surface thereof) are being developed, while practical problems have not however as yet been solved.

On the other hand, research efforts have suddenly increased which propose a technique of, by the utilization of anionicity of oligonucleotide, bonding oligonucleotide to a cationic natural protein or a cationic synthetic poly-amino acid, and delivering the resultant ionic complex to or into target cells (Nature, 271, 130–135 (1978), J. Biol. Chem., 262, 4429–4432 (1987), J. Biol. Chem., 263, 14621–14624 (1988), Proc. Natl. Acad. Sci. USA, 87, 3410–3414 (1990)). This technique is based on the fact that oligonucleotide is bonded in terms of charge to a cationic side chain of amino acid such as $\epsilon$-amino group of lysine (Lys) residue, for example, and forms a relatively stable complex (Lemaitre, M., et al., Proc. Natl. Acad. Sci. U.S.A., 84, 648–651 (1987)). There is however a problem in that formation of these complexes leads to generation of precipitation. In all these studies, therefore, a limit is that complexes are cationic heterogeneous ones.

For example, poly-L-Lys (PLL) is a well-known drug carrier (H. J. P. Ryser and W. C. Shen, Proc. Natl. Acad. Sci. U.S.A., 75, 3867–3879 (1978)). It is known that the complex of PLL and oligonucleotide is biologically very stable, and formation of complex with PLL makes oligonucleotide present stably against nuclease (B. Bayard, et al., Eur. J. Biochem., 151, 319–325(1985)). However, the mixing concentrations in bonding of both PLL and oligonucleotide are limited by the problem of precipitation. This in contrast suggests a possibility that a solution of the complex-precipitation problem increases their mixing concentrations, thus leading to an improved stability of oligonucleotide.

In addition, it is reported that uptake of an oligonucleotide into cell is promoted by forming it to a complex with PLL (Wu, G.Y. and Wu, C.H., J. Biol. Chem., 27, 887–892 (1988)). There is available another report showing the fact that partial chemical modification of PLL increases specificity of oligonucleotide to various cells (E. Wanger, et al., Proc. Natl. Acad. Sci. U.S.A., 87, 3410–3414 (1990)). While its action mechanism has not as yet been clarified, a report demonstrates that PLL exerts an effect on cell membranes to assist interporation of oligonucleotide, and another, that the complex formed by covalent bond of PLL and oligonucleotide increases consequently affinity to cell membranes (M. Fechheimer, et al., Proc. Natl. Acad. Sci. U.S.A., 84, 84633–8467 (1987)). The problem of precipitation as described above has not as yet been solved even with these reports.

As another serious problem, many reports point out cytotoxicity of PLL (J. P. Leonetti, et al., Bio-conjugate Chem., 1, 149–153 (1990)) Zhou, et al. compare a complex of poly-D-Lys (PDL), which is a stereoisomer of PLL, with oligonucleotide and that with PLL, and report that, as a result, the complex of PDL and oligonucleotide is biologically more stable than that with PLL, but is more toxic to cells (X. Zhou, et al., Biochem. Biophys. Acta, 1065, 8–14 (1991)). Although it is thus ascertained that the oligonucleotide complex with PLL is less cytotoxic than that with PDL, the problem of cytotoxicity has not as yet been solved. From the point of view of cytotoxicity, a report points out that PLL having a molecular weight of up to 14,000 exhibits no cytotoxicity (J. P. Leonetti, et al., Bio-conjugate Chem., 1, 149–153 (1990)). This complex is not however suitable as a drug carrier because of the problem of metabolism.

Degols, et al. synthesized an antisense oligonucleotide complementary to the mRNA of tat gene of HIV (Human Immunodeficiency Virus)-1 genome, and studied the tat gene inhibiting effect of the oligonucleotide complex with PLL. They thus ascertained that, in vitro, the complex demonstrated an activity more than 100 times as high as that of antisense alone (P. Degols, et al., Antiviral Res., 17, 279–281 (1992)). Simultaneous use of PLL can thus be deemed to have a gene inhibiting effect of the antisense oligonucleotide.

Under the present circumstances, however, the complex of PLL and oligonucleotide involves a serious problem of very easy agglomeration (J. P. Leonetti, et al., GENE, 72, 323-332 (1988)). For this reason, it has been believed difficult to apply such a cationic natural protein and cationic synthetic poly-amino acid to organism as a drug carrier. Under these circumstances, there has been an increasing demand for the development of a novel oligonucleotide carrier to be transported into body, free from precipitation even after formation of a stable complex.

DISCLOSURE OF INVENTION

The present invention was developed in view of the circumstances as described above and has an object to provide a novel poly-amino acidic oligonucleotide-carrier, which overcomes the defects of the prior art that a cationic polymer compound such as PLL tends to generate precipitate through combination with anionic oligonucleotide, and a complex of such a compound and oligonucleotide formed with low mixing concentrations free from precipitation is cationic and has a cytotoxicity, permits configuration of a complex formed into a homogeneous system and can effectively improve the function thereof as a drug carrier.

The present invention provides, as means to solve the above-mentioned problems, a poly-amino acidic oligonucleotide carrier comprising a poly-lysine:serine random copolymer.

For the carrier of the present invention, a preferable embodiment is that the ratio of lysine:serine is from 5:1 to 1:3 and a weight-average molecular weight is from 3,000 to 35,000.

The poly-amino acidic carrier of the present invention forms, through bonding with oligonucleotide, a homogeneous and stable complex, and efficiently releases an oligonucleotide drug in human cells (pH=5.0).

BRIEF DESCRIPTION OF DRAWINGS

The file of this patent contains at least one color photograph. Copies of this patent with color photograph(s) will be provided by the Patent and Trademark Office upon request and payment of the necessary fee.

FIGS. 1 (a) and (b) are primary structural formulae showing oligonucleotides DRD12 and R32 used in the examples.

FIGS. 7 (a) and (b) illustrate the results of electrophoresis of R32 after reaction with PLS (3/1) and PLS (1/1) respectively.

BEST MODE FOR CARRYING OUT THE INVENTION

Figure 2:
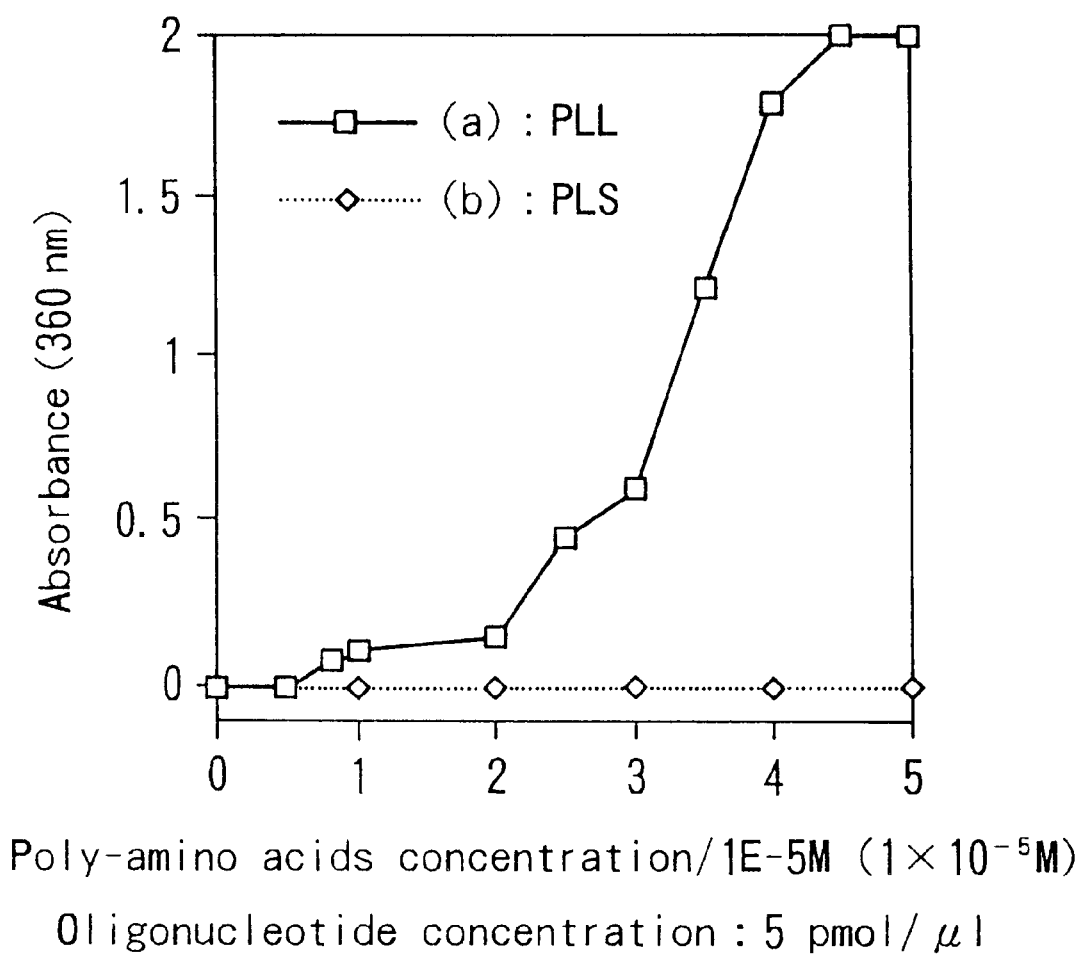
FIG. 2 illustrates the relationship between concentration of poly-amino acids having formed an ionic complex with oligonucleotide and absorbance of the complex.

The poly-amino acids, which is a poly-amino acidic compound comprising a poly-lysine:serine random copolymer, is useful as an in vivo carrier for an oligonucleotide drug such as an antiviral agent.

The poly-amino acidic carrier of the present invention is cationic by being inserted serine (Ser) of which side chain is much hydrophilicity, and forms a stable ionic complex with oligonucleotide without causing precipitation. At an acidic pH condition, furthermore, the bonded oligonucleotide is efficiently discharged.

Such a poly-amino acidic carrier can be expressed, for example, by the following formula. In this formula, the number of Ser residues and the inserted positions are not limited, and m and n are integers. The ratio Lys:Ser should be within a range of from 5:1 to 1:3, or more preferably, from 3:1 to 1:1:

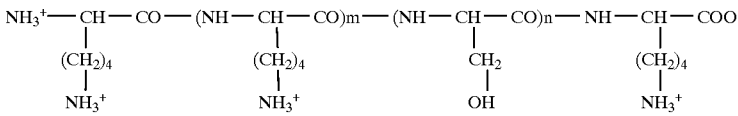

This compound can be prepared by any of the conventional methods (Rajendra, B. R., et al., Human Genetics, 55, 3633 (1980); Lim F. and Sun, A., M. Science, 210, 908 (1980).

EXAMPLE

Now, the present invention will be described in further detail by means of examples. It is needless to mention that the present invention is not limited by these examples.

In the examples described below, the following oligonucleotides were employed for forming a complex with the carrier. The two kinds of oligonucleotide shown in FIGS. 1 (a) and (b) were synthesized with the use of a DNA synthesizer (made by Applied Biosystems Company; type 380B or type 392). In FIG. 1, adenine-nucleotide is represented as A, guanine-nucleotide, as G, cytosine-nucleotide, as C, and uracil-nucleotide, as U. These were synthesized by the phosphoamidite method using t-butyldimethylsilyl group as the protecting group of 2'-hydrochloric group (Nucleic Acid Res., Vol. 17, 7059–7071 (1989))

FIG. 1 (a) shows a linear chimera oligonucleotide comprising twelve bases (DRD12). While substantial portions of the main chain consist of DNA, only three GUC bases near the center comprise RNA. FIG. 1 (b) shows ribonucleotide comprising 32 bases (R32) which is conjectured to form a partially dense secondary structure.

These models of oligonucleotide were purified in accordance with a method described in a reference (Nucleic Acid Res., Vol. 19, 5125–5130 (1991)).

In addition, known plasmid pU119 (3162 base pairs) was used as an oligonucleotide having a large molecular weight.

Labels of poly-amino acid and oligonucleotide

The PLL of Lot. 111H-5520; MW=3,000 Poly-L-Lys-Hydrobromide (PLL ①) by Sigma was mainly used for a control. Also, Poly-L-Lys-Hydrobromides of Lot. 51H-5516; MW=4,600 (PLL ②), Lot.72H-5539; MW=20,500 (PLL ③), and Lot. 111H-5506; MW=37,200 (PLL ④) were used for controls. Examples of poly-Lys: Ser random copolymer (PLS) include Sigma's Lot. 30H-5525; MW=21,800 Poly-(Lys:Ser=3:1)-Hydrobromide [PLS(3/1)] and chemically synthesized MW=30,000 Poly-(Lys:Ser=1:1)-Hydrobromide [PLS(1/1)].

All these poly-amino acids were dissolved by a phosphate buffer solution (pH=7.2) having an ionic strength of 0.02. Labelling of $^{32}p$ of oligonucleotide was made by mixing 27.3 $\mu l$ of oligonucleotide (1.83 OD, 5 pmol), 15.7 $\mu l$ of autoclaved purified water, 5 $\mu l$ of ×10 kinase buffer solution (250 mM tris hydrochloric acid buffer solution: pH=7.6, 100 mM DTT, 100 mM $MgCl_2$), 1 $\mu l$ of T4 polynuclease (10 units/$\mu l$), and 1 $\mu l$ of $\gamma\text{-}^{32}p$ ATP, and then reacting for an hour at 37° C.

Measurements of absorbance, formation of complex, and generation of precipitation Turbidity or generation of precipitate caused by the formation of the ionic complex of poly-amino acids and oligonucleotide was spectroscopically studied by measuring absorbance at 360 nm of the solution. The results are shown in FIG. 2. The concentration of oligonucleotide was 5 pmol/$\mu l$. Respective concentrations of charge neutralization in the formation of the ionic complex were calculated from the numbers of charges calculable from the molecular weights of poly-amino acids and oligonucleotide.

The results of absorbance measurement demonstrate that, when using PLL ① (MW=3,000) as poly-amino acids, turbidity or precipitation was observed (FIG. 2, a) near a PLL concentration at which formation of a complex was anticipated. When changing the molecular weight of PLL (4,600, 20,500 and 37,200), i.e., for PLLs ②, ③ and ④, the results were the same. When using PLS (3/1) random copolymer of the present invention containing about 30% hydrophilic Ser in PLL, in contrast, charge was neutralized, and no turbidity was observed even at a concentration at which formation of a completely ionic complex was anticipated (FIG. 2, b). Even at a higher concentration, the mixed solution was homogeneous. This is attributable to the increase in hydrophilicity of the formed complex resulting from insertion of Ser residues into PLL, and suggests a high effectiveness of PLS of the present invention as a biological carrier.

Electrophoresis

Figure 3:
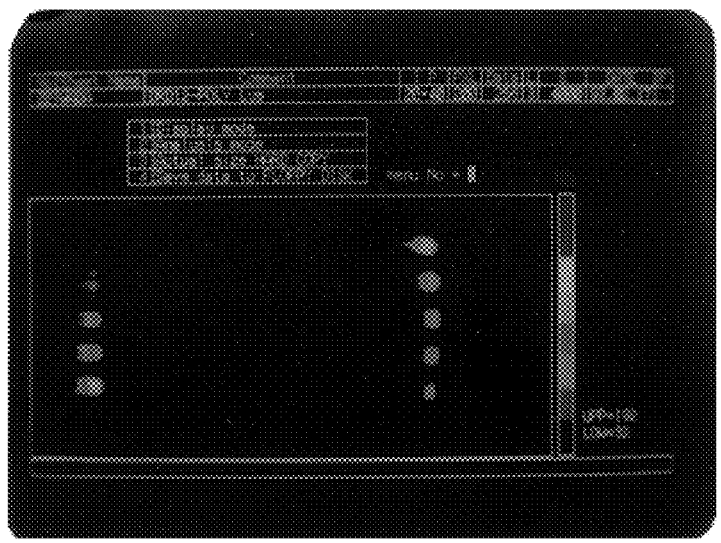
FIG. 3 illustrates the results of electrophoresis of oligonucleotide having formed a complex with PLS carrier of the present invention.

Oligonucleotide exhibits electrophoresis in the positive charge direction because of the negatively charged phosphate group. By adding positively charged poly-amino acids to negatively charged oligonucleotide, negative charge of oligonucleotide is inhibited with the increase in the concentration of poly-amino acids, thus resulting in a decrease in the mobility of oligonucleotide. Mobility was therefore evaluated by adding PLS (3/1) to oligonucleotide DRD12 for bonding and then observing electrophoresis of the resultant mixture. The results are shown in FIG. 3. All the experimental operations for complexes were carried out after a sufficient reaction of the poly-amino acids and oligonucleotide which were stirred for about 15 minutes after mixing.

As shown in FIG. 3, electrophoresis resulted in a decrease in mobility of oligonucleotide along with an increase in PLS concentration. Upon formation of a complex neutralized in terms of electric charge, no electrophoresis of oligonucleotide was observed. Their mixing concentrations upon formation of the complex was estimated on the basis of these results.

Membrane separation and complex forming concentration

Figure 4:
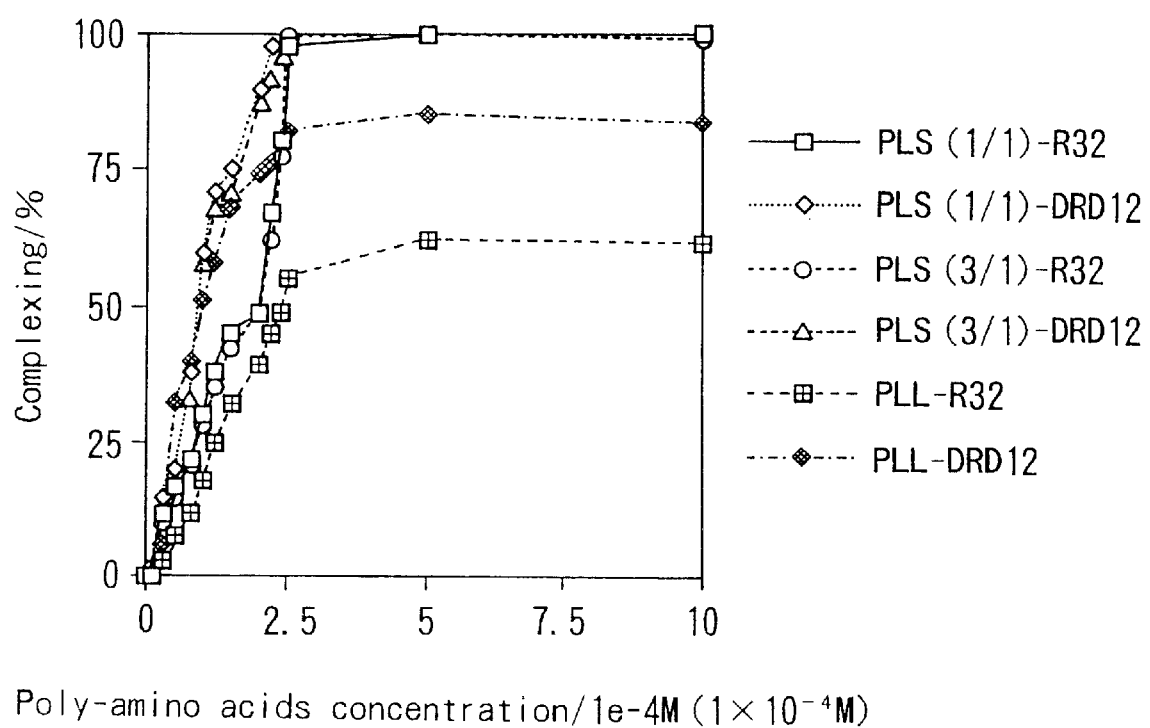
FIG. 4 illustrates the concentrations of poly-amino acidic carrier for forming a complex with oligonucleotides R32 and DRD.

An ultrafiltration tube having a fractionating membrane through which the formed complex can not pass (a centrifugal tube with a limited ultrafree C3-GC uFC3 TGC00 filter, made by Nippon Millipore Company) was previously labelled with $^{32}p$-ATP and was filled with oligonucleotide of which $^{32}p$ content had been measured. This solution and poly-amino acids solution were mixed at various ratios, and then each mixture was placed in the tube for centrifugal separation to measure the $^{32}p$ content in free oligonucleotide in the filtered solution. Finally, the quantity of the formed complex was directly measured while taking account of the $^{32}p$ content in the filtered solution relative to the initial content of $^{32}p$. The results are illustrated in FIG. 4 which shows the results of complex formation, for PLL ①, PLS (33/1) and PLS (1/1), with oligonucleotide DRD1 and R32 shown in FIG. 1.

The measured complex forming concentrations very well agreed with values determined from the measurements mentioned above of absorbance and electrophoresis. In the case with PLS, no turbidity was observed in the complex solution.

The complex forming concentrations of oligonucleotide and poly-amino acids were limited from these results.

In general, it is known, as compared with a linear chain, that oligonucleotide forming a secondary structure such as a stem loop structure is hard to bond to a target antisense molecule having a stem region. This can naturally be conjectured also for the carrier of the present invention. Therefore, the extent to which the molecular weight and three-dimensional structure of oligonucleotide effect on bonding with poly-amino acids was investigated. This was accomplished by the measuring technique based on membrane separation, which comprised using two kinds of oligonucleotide (a) and (b) shown in FIG. 1, and seeing how much complex was formed from what concentrations of oligonucleotide and poly-amino acids.

In the formation of a complex with PLL, a difference was observed between the two kinds of oligonucleotide. Along with the increase in the PLL concentration, formation of the complex of DRD12 and PLL was accelerated to reach finally a quantity of complex formation (association/%) of 80%. That of the complex of PLL and R32 was in contrast about 50% near a high PLL concentration. As compared with a linear-chain oligonucleotide, it is more difficult for secondary-structure oligonucleotide to bond to poly-amino acids having Lys as the main chain.

Figure 5:
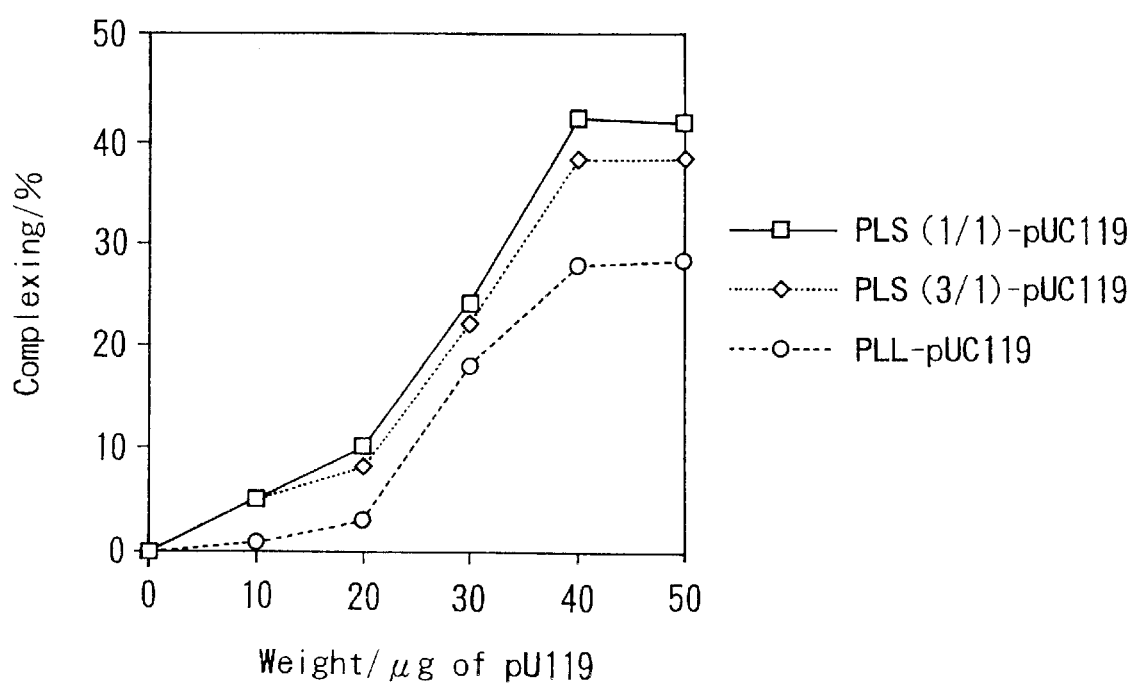
FIG. 5 illustrates the concentration of poly-amino acidic carrier and oligonucleotide pU119.

On the other hand, conformation of oligonucleotide exerted no effect on bonding of oligonucleotide to PLS of the present invention. In all cases, bonding of PLS to oligonucleotide proceeded with the increase in the PLS concentration, to finally reach a quantity of complex formation of PLL-DRD12 or PLS-R32 of 100%. Particularly, PLS (1/1) containing Lys and Ser in equal contents rapidly formed a 100% complex with DRD12 or R32. This is considered attributable to the fact that insertion of Ser residues having a flexible skeleton increases freedom of PLS as a whole, thus permitting as a result avoidance of disturbance to bonding with oligonucleotide having a specific three-dimensional structure. It was thus clarified that, at least regarding conformation of oligonucleotide, the novel carrier of the present invention did not limit drug oligonucleotide. This result suggests that the carrier of the present invention is particularly useful for transport in vivo of an antisense drug or a liposome drug for which research data have recently been increasing, A similar study was carried out on formation of a complex of poly-amino acidic carrier with plasmid pU119 (3162 base pairs) having a far higher molecular weight than the above-mentioned oligonucleoctide DRD12 (12 bases) and R32 (32 bases). Results were as shown in FIG. 5: the carrier PLS of the present invention exhibited a significantly higher complex forming ratio (about 40%) than the conventional PLL carrier (about 30%) with oligonucleotide (pU119) having a high molecular weight, although it showed a lower complex forming ratio than DRD12 or R32 having a low molecular weight. This result demonstrates that the carrier of the present invention is well applicable for transport in vivo of a plasmid expression vector.

Capillary electrophoresis

From the above-mentioned results of the electrophoresis test (FIG. 3), it is expected that the complex of PLS and oligonucleotide has no charge. This result was therefore further clearly confirmed by applying the complex to capillary electrophoresis (multi-channel capillary electrophoresis apparatus: CAPI-3000, having an MCPD-3600 Spectro Multi-Channel Detector, made by Otsuka Electronics Company). An Si-coated capillary tube (anion charged) was employed.

Figure 6A:
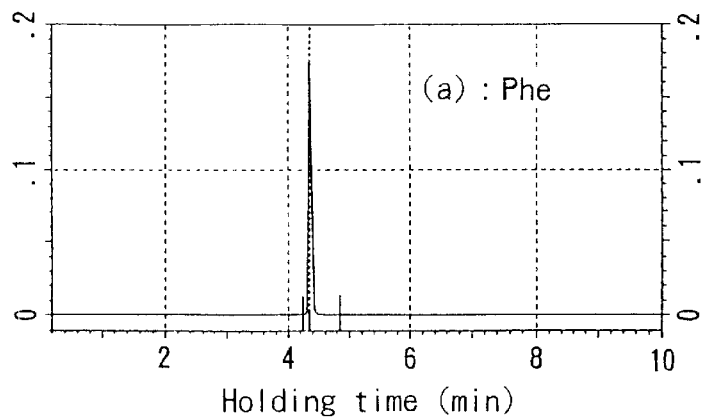
FIGS. 6 (a), (b) and (c) illustrate the respective results of capillary electrophoresis of poly-amino acidic carrier.
Figure 6B:
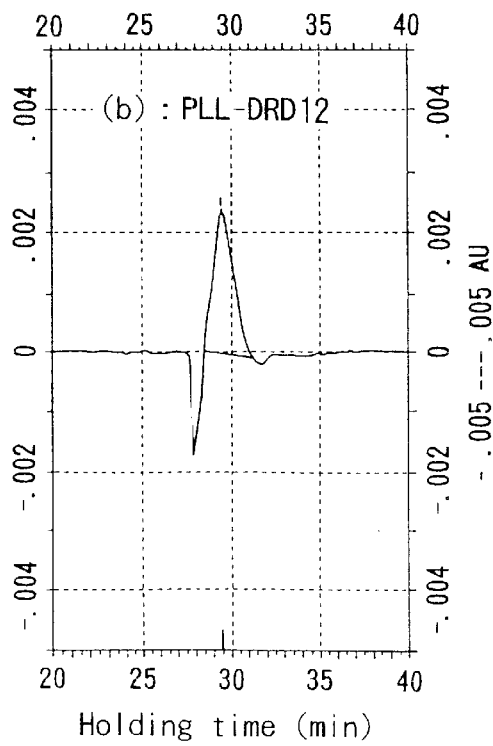
Figure 6C:
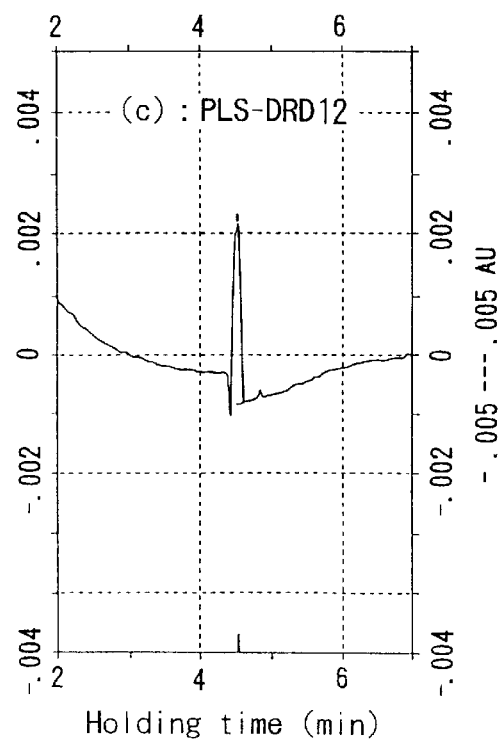

The results are shown in FIGS. 6 (a), (b) and (c) (pherogram at 200 nm). Under these conditions, a peak of phenylalanine (Phe) having no charge was detected in a holding time of 4.35 minutes (a). A peak of PLL and oligonucleotide was detected in 29.46 minutes (b). This means that, because of the positive charge of the complex, its bonding to capillary is caused, thus resulting in a delay in peak detecting time relative to Phe.

The peak of the complex of PLS (3/1) and oligonucleotide was observed in a holding time (4.52 minutes) close to that of Phe having no electric charge (c). This result revealed that the complex of PLS and oligonucleotide does not bring about electric charge.

Since the effect of charge (mainly positive charge) on an organism is considered important when evaluating a carrier system, the PLS carrier having no charge is expected to have a low toxicity to cells, and is suggested to be significant as a novel in vivo drug carrier.

Stability of oligonucleotide

The effect of the formation of an ionic complex on stability of oligonucleotide was evaluated by the following manner in human serum.

Solutions of PLS (3/1) and PLS (1/1) (concentration:$1\times 10^{-4}$M) were prepared by diluting a PLS stock solution adjusted to 1E-4M ($1\times 10^{-4}$) by means of a phosphate buffer solution with the same buffer solution. Then, each of the resultant solution was added to a solution (concentration: 0.25 $\mu g/\mu l$) of oligonucleotide labelled with $^{32}$p-ATP (ribozyme R32), and complex solutions of various mixing ratios were prepared.

After mixing the complex solution of PLS and oligonucleotide while adjusting the amount of addition so as to achieve a final concentration of the human serum solution of 90%, and the resultant solution was incubated at 37° C. Sampling solution taken at an appropriate timing was transferred, after adjusting pH to about 5.0 by the addition of a necessary amount of 1N hydrochloric acid, into an ultrafiltration tube (centrifugal tube with a limited ultrafree C3-GC UFC3 TGC00 filter, made by Nippon Millipore Company) having an amount of membrane fraction molecular weight of 10,000. After removing RNase through centrifugal separation at 5,000 rpm for 15 minutes, the filtered solution was stored at −80° C. until analysis. Upon analysis, these samples were melted at the room temperature, and then subjected to electrophoresis (constant voltage of 2,000 V, for 24 hours) by means of 20% polyacrylamide denatured gel.

Figure 8:
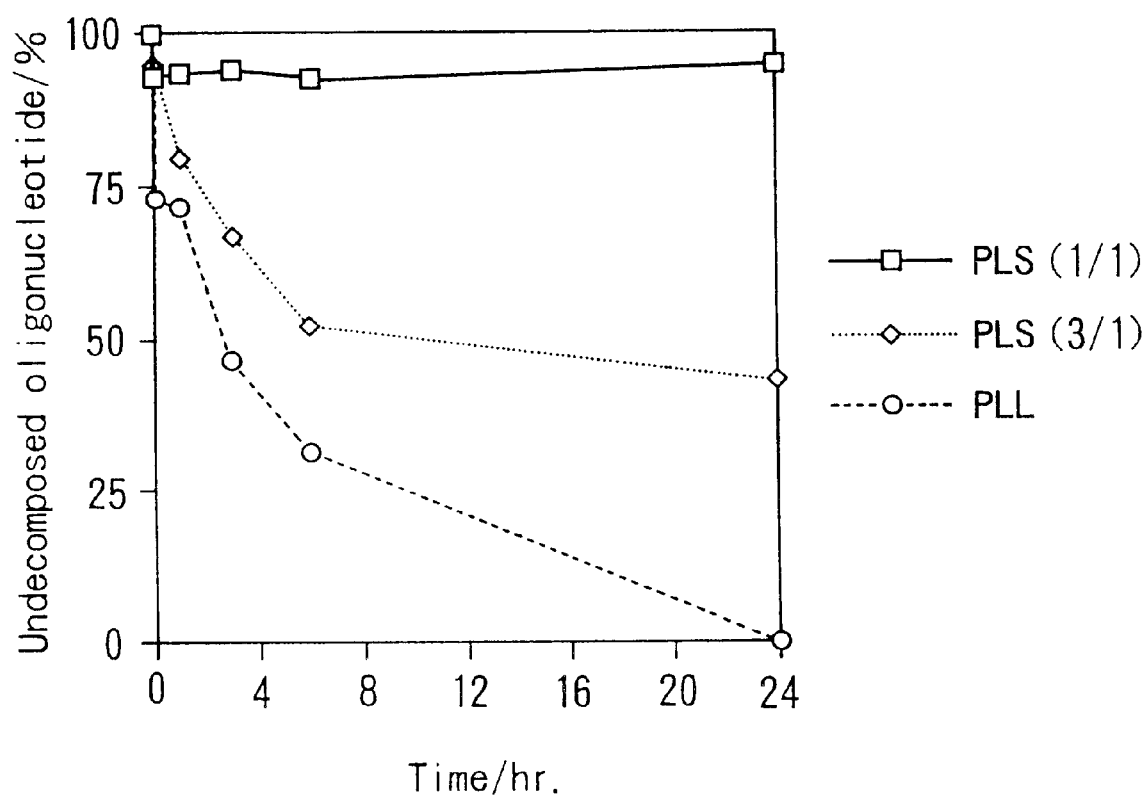
FIG 8 represents the undecomposition ratio with time in human serum of oligonucleotide having formed a complex with poly-amino acidic carrier.

The results are shown in FIGS. 7 (a) and (b). FIG. 7 (a) represents the results of PLS (3/1): the five lanes show decomposition patterns of R32 present in human serum upon the lapse of the individual times. The bands observed on top of the gel are undecomposed R32, and slight bands observed at the bottom are R32 decomposed by ribonucleases. As is clear from this result of electrophoresis, while decomposition of R32 is not observed until the lapse of 0.08 hours when using PLS (3/1), the amount of decomposed R32 increased with time. The amount of undecomposed R32 upon the lapse of 24 hours was less than a half that upon the lapse of 0.08 hours. On the other hand, FIG. 7 (b) represents corresponding results for PLS (1/1): undecomposed R32 upon the lapse of 24 hours had a band strength of almost the same level as that upon the lapse of 0 hour, and almost no lower band which suggested the presence of R32 dissociated from the carrier was observed. Finally, residual RNA was measured with a bio-image analyzer (made by Fuji Film Company, BA100), and the measured result was adopted as the amount of undecomposed oligonucleotide. As a control, similar test was carried out on a PLL solution. The results of these studies are shown in FIG. 8.

In human serum having a final concentration of 90%, free oligonucleotide (not forming a complex) is usually decomposed in a very short period of time. It was in contrast confirmed that oligonucleotide having a complex with poly-amino acidic carrier became harder to be decomposed. However, oligonucleotide having formed a complex with PLL is decomposed with time, and no complete oligonucleotide was observed after the lapse of 24 hours.

In the case of oligonucleotide protected by the formation of a complex with PLS (3/1), in contrast, 50% was stably present even after the lapse of 24 hours. For oligonucleotide having formed a complex with PLS (1/1) rich in Ser residues, more than 90% were stably present even after the lapse of 24 hours.

These results demonstrate that the cationic PLS carrier of the present invention, when bonded with an oligonucleotide drug, does not generate precipitate, and large contribute to stabilization of the oligonucleotide drug administered in vivo. It was also suggested clearly that the increase in the Ser residues content effectively acted on the improvement of functions of PLS as a carrier.

Release of oligonucleotide

Release of oligonucleotide from the once formed ionic complex was made possible by altering pH of the system.

It is well known that PLL, while presenting a 100% helix structure under strong alkaline conditions, takes almost a 100% random coil structure under acidic conditions. Paying attention to the feature of PLL of being sensitive to pH, PLS, a random copolymer of PLL, was expected to be sensitive to pH as well. As a result of a circular dichroism measurement, PLS induces more helix structures than PLL near pH 7, but the helix content at a pH of up to 5 was almost on the same level as that of PLL. This suggests a possibility that, in blood (ph=7.0), many helix structures of PLS protect oligonucleotide from nuclease, and when lysosome (pH=5.0) at which it is incorporated into cells is reached, the oligonucleotide drug is promptly released.

On the basis of the above-mentioned results of measurement of absorbance, electrophoresis and membrane separating measurement, each of PLS (3/1) and PLS (1/1) solutions was mixed with an oligonucleotide R32 solution (5 pmol/ml) labelled with $^{32}$p-ATP, and solutions of complexes thereof were prepared. A complex solution in which the complex was in an environment within a pH range of from about 3 to about 10 was prepared by adjusting pH through addition of 1N hydrochloric acid or 1N NaOH. Each of these solutions was transferred into an ultrafiltration tube (centrifugal tube with a limited ultrafree C3-GC UFC3 TGC00 filter, made by Nippon Millipore Company) and centrifugally separated at 5,000 rpm for 15 minutes.

Figure 9:
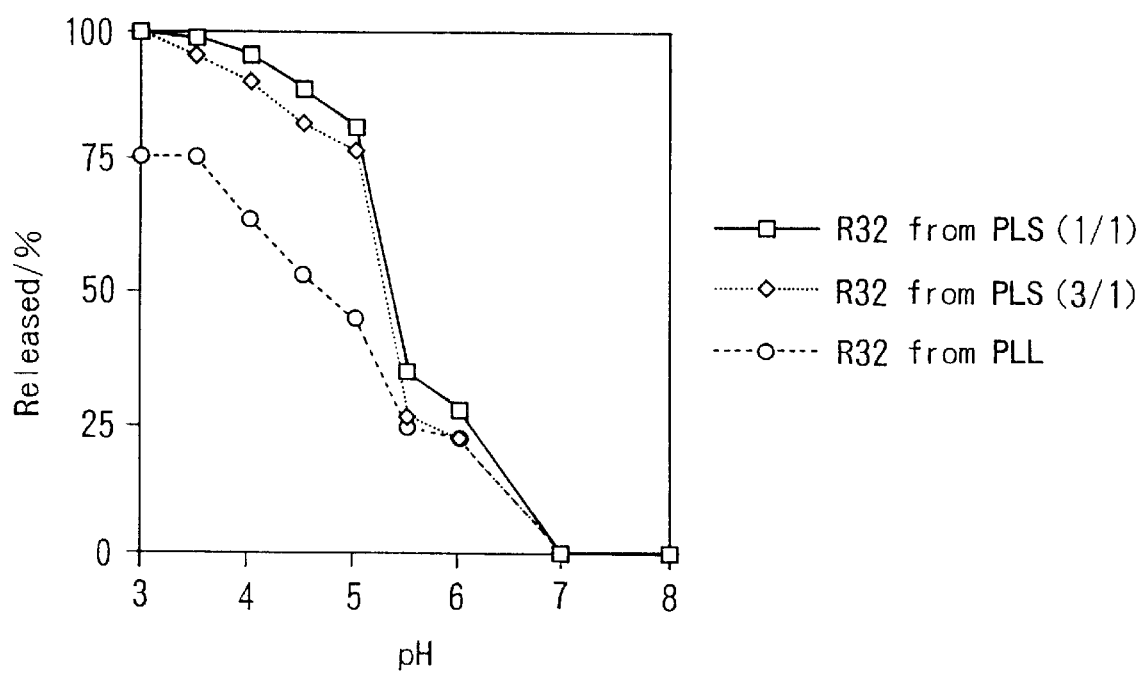
FIG. 9 illustrates the relationship between the discharge ratio and pH for oligonucleotide R32 having forming a complex with poly-amino acidic carrier.

The amount of $^{32}$p in the filtered solution was measured, and the amount of free oligonucleotide was determined with due regard to the amount of $^{32}$p in the filtered solution relative to the initial amount of $^{32}$p. The results are shown in FIG. 9.

Oligonucleotide having formed a complex with polyamino acidic carrier begins to be released from the carrier at a pH of up to 6. At the proximity to pH of 3 on the acidic side, the PLS carrier of the present invention showed a dissociation of oligonucleotide of 100%, whereas the PLL carrier showed a dissociation of only 75%. Particularly, in the case of pH of about 5.0, which is the same condition as for lysosome, there was observed a remarkable difference between PLL and PLS. As is evident from the above description, oligonucleotide such as virus-inhibiting gene delivered into cell by the PLS carrier of the present invention, leaves the PLS carrier under the effect of pH of lysosome, and can thus fully display its own functions.

Figure 10:
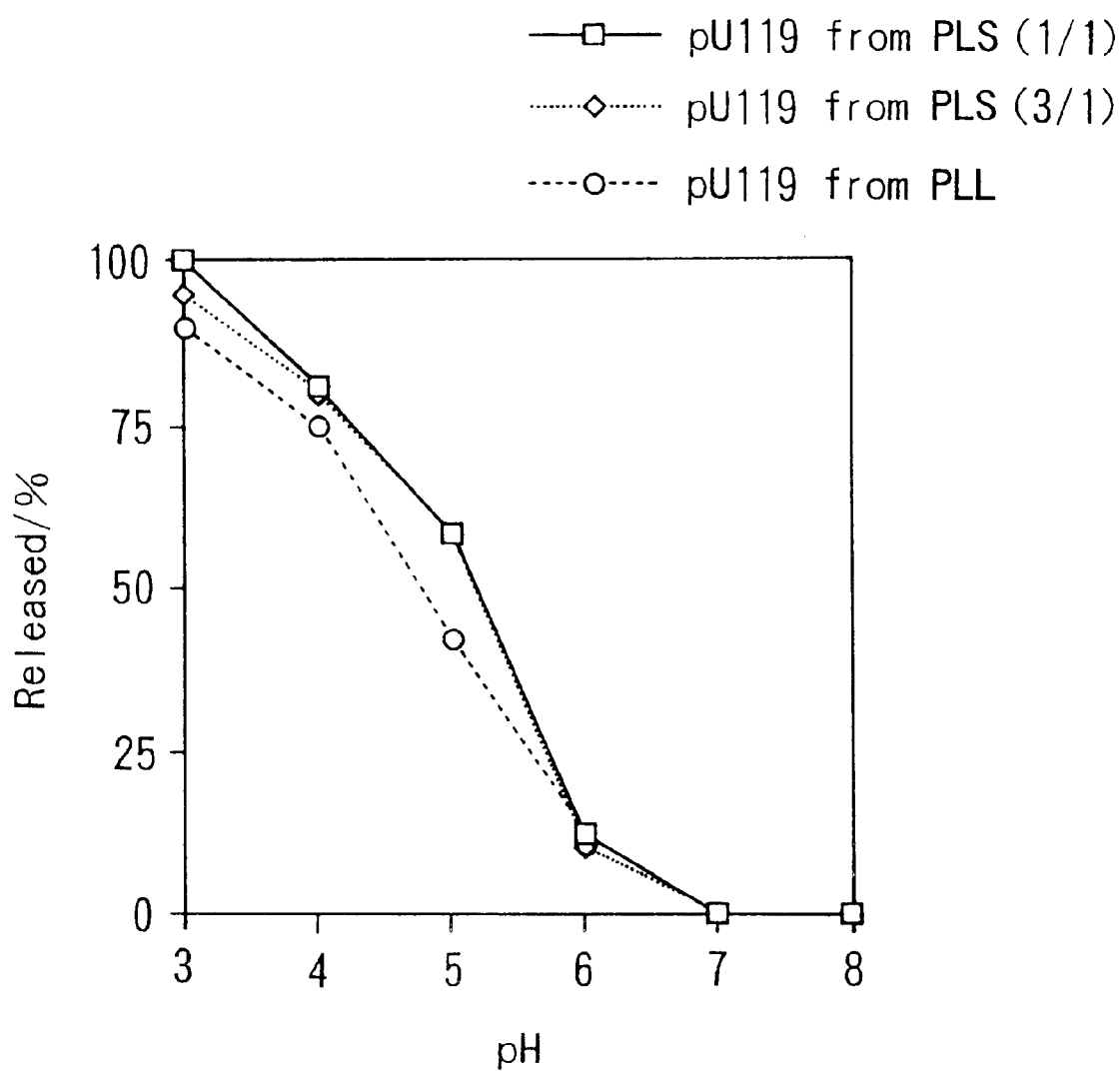
FIG. 10 illustrates the relationship between the discharge ratio and pH for oligonucleotide pU119 having formed a complex with poly-amino acidic carrier.

Similar study was carried out also on oligonucleotide pU119 having a high molecular weight. The results are as shown in FIG. 10: only PLS (1/1) in the acidic region (pH=3) released 100% pU119. Although not 100%, PLS (3/1) showed a more excellent releasing function than PLL. With a pH of 5, the same condition as lysosome, the difference between PLS and PLL was remarkable. It was confirmed from this result that the carrier PLS of the present invention was useful not only for an antisense drug or a ribozyme drug, but also for transport in vivo of a plasmid expression vector or the like.

Industrial Applicability

Poly-amino acidic oligonucleotide-carrier of the present invention is banded to oligonucleotide without causing precipitation, and smoothly releases the bonded oligonucleotide in cells. It is therefore useful as an in vivo transport carrier of an oligonucleotide drug against various genetic diseases and viral diseases such as AIDS. It also makes a great contribution in the creation of various useful animals and plants by genetic engineering technique, including virus-resistant plants.

What is claimed is:

1. An ionic complex comprising a cationic poly-lysine: poly-serine random copolymer and an anionic oligonucleotide, wherein the anionic oligonucleotide is ionically bonded to the cationic poly-lysine: poly-serine random copolymer.

2. The ionic complex according to claim 1, wherein the ratio of lysine to serine in the random copolymer is within a range of from 5:1 to 1:3.

3. The ionic complex according to claim 1, wherein the random copolymer has a weight average molecular weight within a range of from 3,000 to 35,000.

4. A method for stabilizing an anionic oligonucleotide, which comprises contacting the anionic oligonucleotide with a cationic poly-lysine:poly-serine random copolymer, wherein the anionic oligonucleotide is ionically bonded to the cationic poly-lysine: poly-serine random copolymer, to thereby stabilize the anionic oligonucleotide.

5. The method according to claim 4, wherein the ratio of lysine to serine in the random copolymer is within a range of from 5:1 to 1:3.

6. The method according to claim 4, wherein the random copolymer has a weight average molecular weight within a range of from 3,000 to 35,000.

* * * * *